(12) United States Patent
Yanagisawa

(10) Patent No.: US 7,932,312 B2
(45) Date of Patent: Apr. 26, 2011

(54) ORGANOSILICON COMPOUND AND PRESSURE-SENSITIVE ADHESIVE COMPOSITION FOR LIQUID CRYSTAL ELEMENT CONTAINING SAME

(75) Inventor: Hideyoshi Yanagisawa, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 105 days.

(21) Appl. No.: 12/275,605

(22) Filed: Nov. 21, 2008

(65) Prior Publication Data

US 2009/0137710 A1    May 28, 2009

(30) Foreign Application Priority Data

Nov. 22, 2007  (JP) ................ 2007-303738
Nov. 22, 2007  (JP) ................ 2007-303739

(51) Int. Cl.
*C08K 5/24* (2006.01)
*C07F 7/04* (2006.01)

(52) U.S. Cl. ...................... 524/264; 556/440

(58) Field of Classification Search ............ 524/264
See application file for complete search history.

(56) References Cited

U.S. PATENT DOCUMENTS

| 4,418,207 A | 11/1983 | Braun et al. |
| 4,808,649 A * | 2/1989 | Gay et al. ............. 524/264 |
| 4,981,986 A | 1/1991 | Yoshioka et al. |
| 6,121,404 A | 9/2000 | Liles |

FOREIGN PATENT DOCUMENTS

| JP | 56-15243 | 2/1981 |
| JP | 63-250390 | 10/1988 |
| JP | 3533446 | 3/2004 |
| JP | 2005-314325 | 11/2005 |

OTHER PUBLICATIONS

Broggini, et al., "Synthesis of Bis-(3,5)pyrazolophanes by Sequential Intermolecular-Intramolecular Nitrilimine Cycloadditions", Tetrahedron, vol. 54, No. 12, pp. 2843-2852, 1998.

* cited by examiner

*Primary Examiner* — Ling-Siu Choi
*Assistant Examiner* — Hui Chin
(74) *Attorney, Agent, or Firm* — Oblon, Spivak, McClelland, Maier & Neustadt, L.L.P.

(57) ABSTRACT

A novel organosilicon compound having a β-ketoester structure and a pressure-sensitive adhesive composition for a liquid crystal element that includes the organosilicon compound are provided. The organosilicon compound is obtained by reacting, in the presence of a transition metal catalyst, a compound represented by a formula (1):

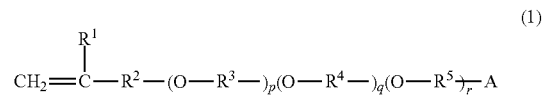

[wherein, $R^1$ represents H or Me, $R^2$ to $R^4$ represent divalent hydrocarbon groups, A represents a group of a formula (i):

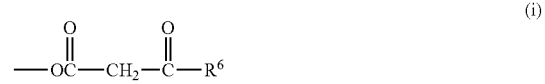

(wherein, $R^6$ represents an alkyl group or a phenyl group), $R^5$ represents a group of a formula (ii):

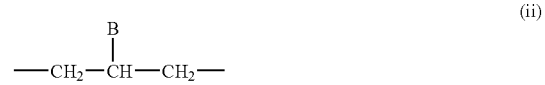

(wherein, B represents OH or a group represented by the formula (i)), and
p, q and r represent integers of 0 to 6] with an alkoxysilane represented by a formula (2):

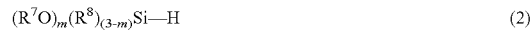

[wherein, $R^7$ and $R^8$ represent monovalent hydrocarbon groups of 1 to 4 carbon atoms, and m represents 1, 2 or 3].

15 Claims, 1 Drawing Sheet

ORGANOSILICON COMPOUND AND PRESSURE-SENSITIVE ADHESIVE COMPOSITION FOR LIQUID CRYSTAL ELEMENT CONTAINING SAME

BACKGROUND OF THE INVENTION

1. Field of the Invention

The present invention relates to a novel organosilicon compound having a β-ketoester structure within the molecule, and a pressure-sensitive adhesive composition for a liquid crystal display device that uses the organosilicon compound as an adhesive improver, or more specifically, a pressure-sensitive adhesive composition for a liquid crystal element that can be detached during production of the liquid crystal display device, but develops increased adhesion over time, and exhibits excellent durability when used under conditions of high temperature and high humidity.

2. Description of the Prior Art

Organosilicon compounds having a β-ketoester structure within the molecule and also containing an alkoxysilyl group within the molecule are already known, and are disclosed, for example, in Patent Reference 1. These compounds are used as metal ion scavengers, surface treatment agents for inorganic materials, interfacial binding agents for composite materials composed of an inorganic material and an organic material, dispersants for inorganic materials, and adhesion improvers for improving the bonding of organic-based adhesives to inorganic substrates. They are also useful as adhesion improvers for primer compositions.

In this manner, β-ketoester structure-containing organosilicon compounds are already in use within organic-inorganic composite materials and organic resin-based adhesives. However, when a conventional β-ketoester structure-containing organosilicon compound is added to a resin or rubber, and is subsequently mixed with an inorganic material such as an inorganic powder like silica, alumina or mica that is added as a filler, the effects of the organosilicon compound in improving the interfacial binding and the dispersion are not entirely satisfactory. Furthermore, when a conventional β-ketoester structure-containing organosilicon compound is added as an adhesion improver to an organic adhesive such as an epoxy-based or urethane-based adhesive, the improvement in adhesion is not entirely satisfactory.

A liquid crystal element is formed from two glass substrates having a transparent electrode on the surface of the glass that contacts the liquid crystal, a liquid crystal material that is used to fill the space between the two glass substrates, and either a polarizing plate, or a laminate composed of a polarizing plate and a retardation plate, disposed on the outside surface of each of the two glass substrates.

In this type of liquid crystal element, each polarizing plate or laminate composed of a polarizing plate and a retardation plate is bonded to the surface of the glass substrate using an acrylic resin-based pressure-sensitive adhesive.

In a production process for a liquid crystal element that uses this type of pressure-sensitive adhesive, if a problem arises during the bonding of the polarizing plate or the laminate composed of a polarizing plate and a retardation plate to the glass substrate, then provided the polarizing plate or the laminate composed of a polarizing plate and a retardation plate is able to be detached from the glass substrate, and a new polarizing plate or laminate composed of a polarizing plate and a retardation plate then re-bonded to the glass substrate, the expensive liquid crystal material and the cell containing the liquid crystal material need not be discarded, and can still be used to produce a liquid crystal element having favorable liquid crystal performance. From this perspective, the pressure-sensitive adhesive is preferably able to be readily released if a problem occurs during the bonding of the polarizing plate, or the laminate composed of a polarizing plate and a retardation plate, to the glass substrate.

In recent years, the range of potential applications for liquid crystal elements has expanded enormously, and includes displays for personal computers, vehicle-mounted liquid crystal monitors, and televisions. As this range of potential applications expands, the environmental conditions in which the liquid crystal elements are used are becoming increasingly severe. Accordingly, the adhesive strength between the polarizing plate, or the laminate composed of a polarizing plate and a retardation plate, and the glass substrate is preferably as strong as possible in order to withstand these environmental conditions, and it is desirable that this superior adhesive strength is maintained over long periods without fluctuation.

The pressure-sensitive adhesive used in bonding the polarizing plates, or the laminates composed of a polarizing plate and a retardation plate, to the glass substrates of the liquid crystal element requires somewhat contradictory properties, in that when a problem occurs during the production process and an attempt is made to detach a polarizing plate or a laminate composed of a polarizing plate and a retardation plate, the polarizing plate or laminate composed of a polarizing plate and a retardation plate should be readily detachable from the substrate without damaging the liquid crystal element, but in contrast, once the liquid crystal element has been supplied for actual use within a practical application, stable adhesive strength should be maintained over a long period.

Conventionally, acrylic resin-based pressure-sensitive adhesives that use an organosilicon compound having a β-ketoester structure within the molecule as an adhesion improver have been reported, for example in Patent Reference 2, as enabling ready detachment from the substrate of the polarizing plate or laminate composed of a polarizing plate and a retardation plate without damaging the liquid crystal element if a problem occurs during the production process, and yet yielding stable adhesive strength that can be maintained over a long period once the liquid crystal element has been supplied for actual use within a practical application. However, even if these known organosilicon compounds having a β-ketoester structure are used, the stability of the adhesive strength over a long period is still unsatisfactory under some of the severe operating conditions now being required, meaning further improvement is required.

[Patent Reference 1] U.S. Pat. No. 4,981,986
[Patent Reference 2] JP 3,533,446 B2

SUMMARY OF THE INVENTION

An object of the present invention is to provide a novel organosilicon compound that addresses the disadvantages and drawbacks associated with the β-ketoester structure-containing organosilicon compounds of the conventional technology described above.

Another object of the present invention is to provide a pressure-sensitive adhesive composition that is particularly suited to bonding a glass substrate to a polarizing plate, or bonding a glass substrate to a laminate of a polarizing plate and a retardation plate. Specifically, this object of the present invention aims to provide a pressure-sensitive adhesive composition for a liquid crystal element that enables either a polarizing plate or a laminate of a polarizing plate and a retardation plate to be bonded reliably and with an appropriate level of adhesive strength to a glass substrate that constitutes part of a liquid crystal element, wherein if, during the production process, this polarizing plate or laminate of a polarizing plate and a retardation plate needs to be detached, detachment can be achieved without damaging the liquid crystal cell of the glass substrate and without leaving residual adhesive on the glass substrate, but once the liquid crystal element has been supplied for actual use within a practical application, a stable and powerful adhesion can be maintained over a long period.

As a result of intensive investigation, the inventors of the present invention discovered that the above objects could be achieved by using an organosilicon compound having a β-ketoester structure obtained by conducting a reaction, in the presence of a transition metal catalyst, between:

an unsaturated group-containing compound having a β-ketoester structure, represented by a formula (1) shown below:

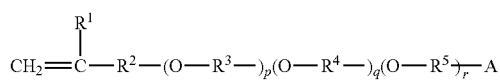
(1)

[wherein, $R^1$ represents a hydrogen atom or a methyl group,
$R^2$ represents a divalent hydrocarbon group of 1 to 10 carbon atoms,
$R^3$ represents a divalent hydrocarbon group of 2 to 10 carbon atoms,
$R^4$ represents a divalent hydrocarbon group of 3 to 10 carbon atoms that is different from $R^3$,
A represents a group represented by a formula (i) shown below:

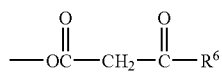
(i)

(wherein, $R^6$ represents an alkyl group of 1 to 10 carbon atoms, or a phenyl group that either has, or does not have, a substituent),
$R^5$ represents a group represented by a formula (ii) shown below:

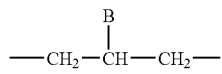
(ii)

(wherein, B represents OH or a group represented by the formula (i)), and
p, q and r each represents, independently, an integer of 0 to 6, provided that p, q and r are not all zero], and
an alkoxysilane represented by a formula (2) shown below:

(2)

[wherein, $R^7$ and $R^8$ each represents, independently, a monovalent hydrocarbon group of 1 to 4 carbon atoms, and m represents 1, 2 or 3].

Furthermore, the inventors of the present invention also discovered that the above objects could be achieved by employing a pressure-sensitive adhesive composition for a liquid crystal element, the composition comprising:

(A) an acrylic polymer, and
(B) an adhesion improver composed of an organosilicon compound having a β-ketoester structure, obtained by conducting a reaction, in the presence of a transition metal catalyst, between:

an unsaturated group-containing compound having a β-ketoester structure, represented by a formula (1) shown below:

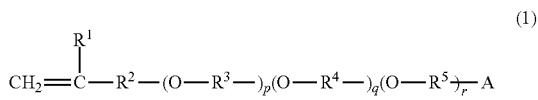
(1)

[wherein, $R^1$ represents a hydrogen atom or a methyl group,
$R^2$ represents a divalent hydrocarbon group of 1 to 10 carbon atoms,
$R^3$ represents a divalent hydrocarbon group of 2 to 10 carbon atoms,
$R^4$ represents a divalent hydrocarbon group of 3 to 10 carbon atoms that is different from $R^3$,
A represents a group represented by a formula (i) shown below:

(i)

(wherein, $R^6$ represents an alkyl group of 1 to 10 carbon atoms, or a phenyl group that either has, or does not have, a substituent),
$R^5$ represents a group represented by a formula (ii) shown below:

(ii)

(wherein, B represents OH or a group represented by the formula (i)), and
p, q and r each represents, independently, an integer of 0 to 6, provided that p, q and r are not all zero], and
an alkoxysilane represented by a formula (2) shown below:

(2)

[wherein, $R^7$ and $R^8$ each represents, independently, a monovalent hydrocarbon group of 1 to 4 carbon atoms, and m represents 1, 2 or 3], wherein
the quantity of the adhesion improver of the component (B) is within a range from 0.001 to 10 parts by mass per 100 parts by mass of the acrylic polymer of the component (A).

The organosilicon compound of the present invention is a novel organosilicon compound that has a β-ketoester structure and an alkoxysilyl group within the molecule, and when added to a resin or a rubber and mixed with an inorganic material, is able to improve the dispersibility of the inorganic material and enhance the interfacial binding effect between the inorganic material and the organic resin. Furthermore, when added to an adhesive or the like, the organosilicon compound of the present invention yields an adhesion improvement effect. Accordingly, the organosilicon compound is useful as a dispersion improver for inorganic materials, an interfacial binding agent, an adhesion improver, and a component for a primer composition.

In a production process for a liquid crystal element, a pressure-sensitive adhesive composition for a liquid crystal element according to the present invention is able to bond a glass substrate to a polarizing plate or a laminate of a polarizing plate and a retardation plate with a satisfactory and appropriate adhesive strength. This adhesive strength does not become excessively powerful even if the adhesive composition is exposed to heat or the like during the production process, but is rather maintained at an appropriate level. As a result, if an adhesion problem occurs during the production process, the polarizing plate or the laminate composed of a polarizing plate and a retardation plate is able to be readily detached from the glass substrate, and if such a detachment is conducted, residual adhesive is unlikely to remain on the substrate, and the detachment operation is very unlikely to damage the glass substrate or the liquid crystal cell.

Moreover, although the pressure-sensitive adhesive composition of the present invention exhibits appropriate levels of adhesion and detachability during the liquid crystal production process, when the completed liquid crystal element is supplied for actual use within a practical application, satisfactory and favorable adhesive strength can be stably maintained over a long period, even if the element is exposed to severe conditions such as high temperature and high humidity, and adhesive faults such as swelling or peeling of the polarizing plate or the laminate composed of a polarizing plate and a retardation plate are unlikely.

DETAILED DESCRIPTION OF THE PREFERRED EMBODIMENTS

Figure 1:
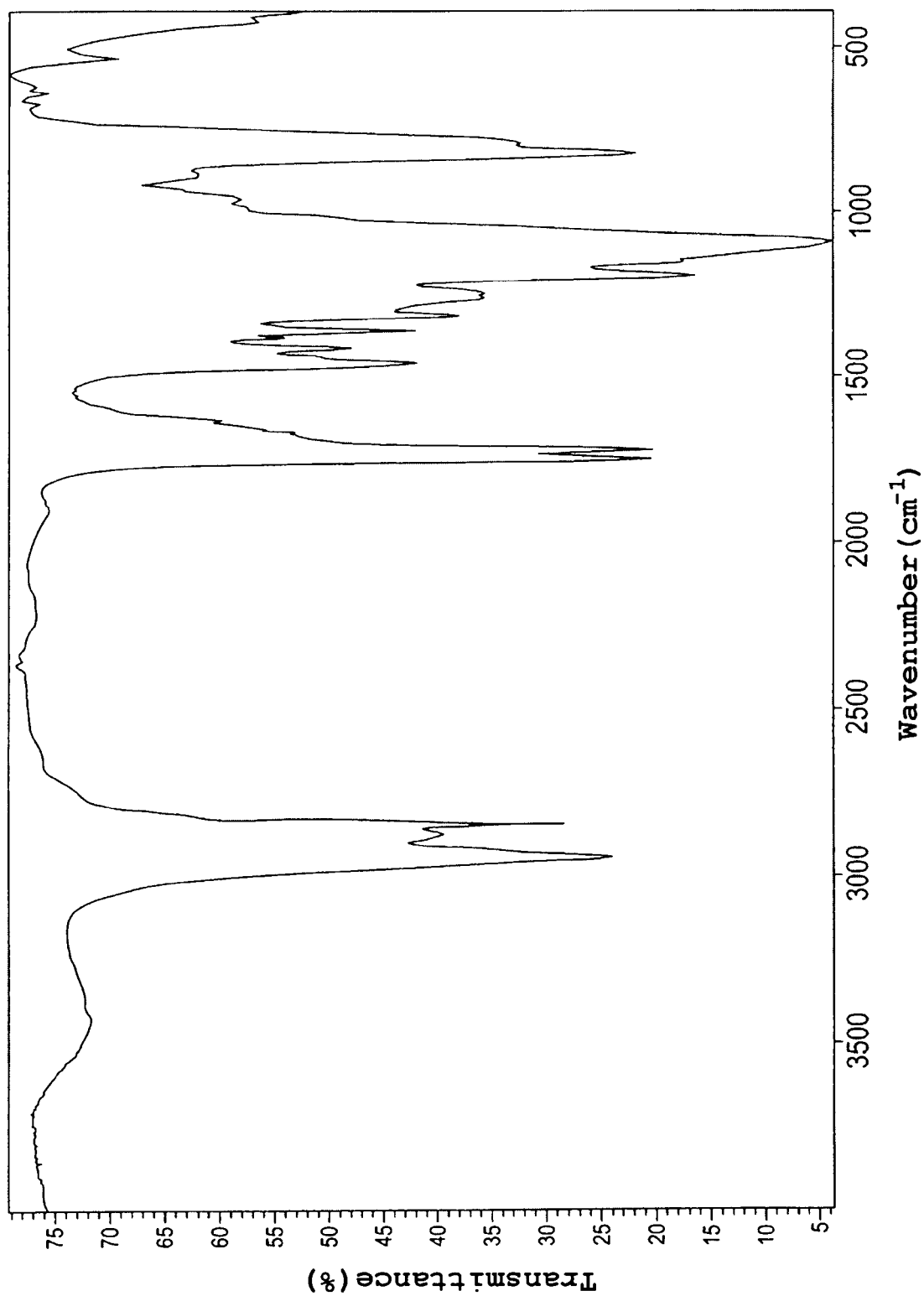
FIG. 1 is a chart showing the infrared absorption spectrum for an organosilicon compound of the present invention obtained in Example 5.

A more detailed description of the present invention is presented below.

An organosilicon compound of the present invention is obtained by reacting an unsaturated group-containing compound having a β-ketoester structure, represented by a formula (1) shown below:

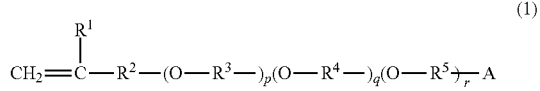

(1)

and an alkoxysilane represented by a formula (2) shown below:

$(R^7O)_m(R^8)_{(3-m)}Si—H$ (2)

in the presence of a transition metal catalyst.

-Unsaturated Group-Containing Compound Having a β-Ketoester Structure-

In the formula (1), which represents an unsaturated group-containing compound having a β-ketoester structure that acts as one reaction component, $R^1$ represents a hydrogen atom or a methyl group, and $R^2$ represents a divalent hydrocarbon group of 1 to 10 carbon atoms, including alkylene groups of 1 to 10 carbon atoms, preferably 1 to 4 carbon atoms, and more preferably 1 to 2 carbon atoms, such as a methylene group, ethylene group, n-propylene group, i-propylene group, n-butylene group, i-butylene group, hexylene group or decylene group, and of these, a methylene group or ethylene group is particularly preferred. $R^3$ represents a divalent hydrocarbon group of 2 to 10 carbon atoms, including alkylene groups of 2 to 10 carbon atoms, preferably 2 to 4 carbon atoms, and more preferably 2 to 3 carbon atoms, such as an ethylene group, n-propylene group, i-propylene group, n-butylene group, i-butylene group, hexylene group or decylene group, and of these, an ethylene group is particularly preferred. $R^4$ represents a divalent hydrocarbon group of 3 to 10 carbon atoms that is different from $R^3$, including alkylene groups of 3 to 10 carbon atoms, preferably 3 to 4 carbon atoms, and most preferably 3 carbon atoms, such as an n-propylene group, i-propylene group, n-butylene group, i-butylene group, hexylene group or decylene group, and of these, an i-propylene group or n-propylene group is particularly preferred.

A represents a group represented by a formula (i) shown below.

(i)

$R^5$ represents a group represented by a formula (ii) shown below.

(ii)

p, q and r each represents an integer of 0 to 6, provided that p, q and r are not all zero.

In the formula (i), $R^6$ represents an alkyl group of 1 to 10 carbon atoms, or a phenyl group that may have a substituent. Examples of the alkyl group include alkyl groups of 1 to 10 carbon atoms, preferably 1 to 6 carbon atoms, and more preferably 1 to 4 carbon atoms, such as a methyl group, ethyl group, n-propyl group, i-propyl group, n-butyl group, i-butyl group, t-butyl group, hexyl group, octyl group or decyl group. Examples of the substituent that may exist on the phenyl group include an alkyl group of 1 to 6 carbon atoms, and preferably 1 to 3 carbon atoms. Accordingly, specific examples of preferred forms of the phenyl group that may have a substituent include a phenyl group, methylphenyl group or ethylphenyl group. Of these, $R^6$ is most preferably a methyl group.

In the formula (ii), B represents OH or a group represented by the formula (i).

Preferred compounds among the compounds represented by the formula (1) are those in which $R^2$ represents an alkylene group of 1 to 4 carbon atoms, $R^3$ represents an alkylene group of 2 to 4 carbon atoms, $R^4$ represents an alkylene group of 3 or 4 carbon atoms which is different from those represented by $R^3$, A represents a group represented by the formula (i) wherein $R^6$ represents an alkyl group of 1 to 4 carbon atoms, a phenyl group, a methylphenyl group or an ethylphenyl group.

More preferred compounds among the compounds represented by the formula (1) are those in which $R^2$ represents a methylene group, $R^3$ represents an ethylene group, $R^4$ represents an i-propylene group or n-propylene group, and A represents a group represented by the formula (i) wherein $R^6$ represents a methyl group.

Representative examples of compounds represented by the general formula (1) include the compounds shown below.

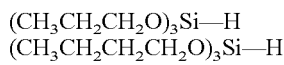

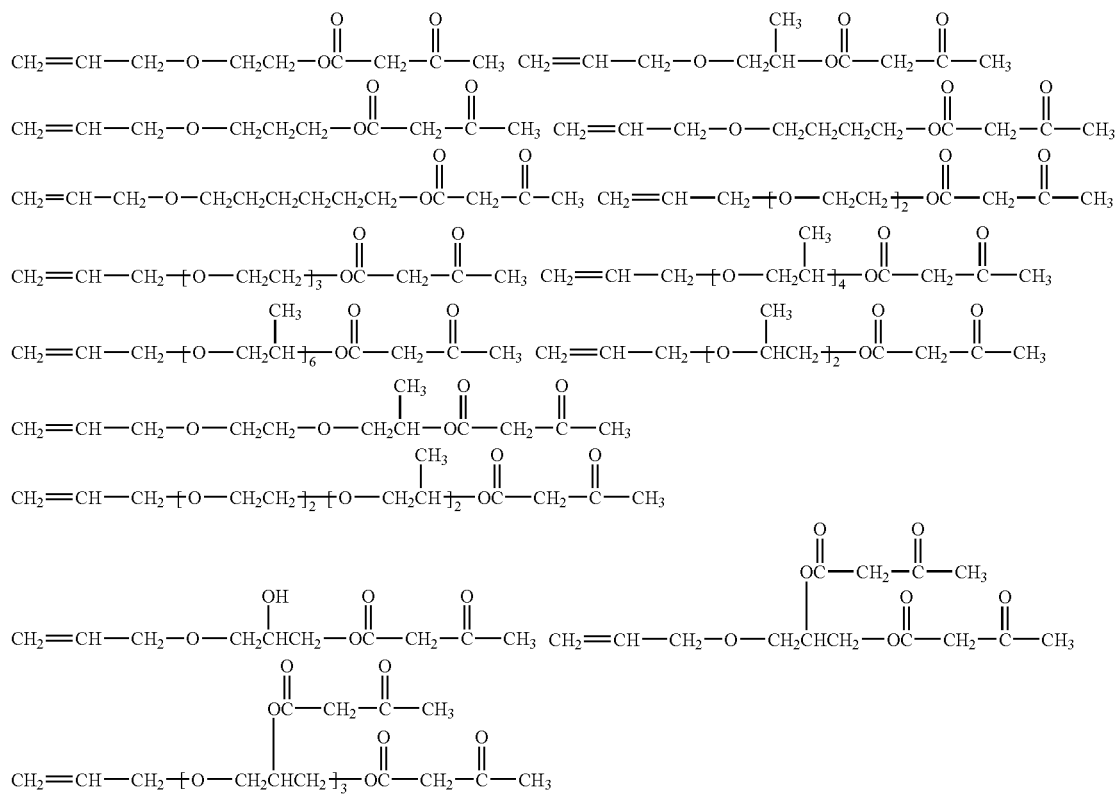

-Alkoxysilane-

In the formula (2), which represents an alkoxysilane that acts as the other reaction component, $R^7$ represents a monovalent hydrocarbon group of 1 to 4 carbon atoms, and preferably represents an alkyl group of 1 to 4 carbon atoms, and more preferably 1 to 2 carbon atoms. Specific examples include a methyl group, ethyl group, n-propyl group, i-propyl group, n-butyl group, i-butyl group or t-butyl group, and of these, a methyl group or ethyl group is particularly desirable.

$R^8$ represents a monovalent hydrocarbon group of 1 to 4 carbon atoms, and preferably represents an alkyl group of 1 to 4 carbon atoms. Specific examples of preferred alkyl groups include a methyl group, ethyl group, n-propyl group, i-propyl group, n-butyl group, i-butyl group or t-butyl group, and of these, a methyl group is particularly desirable.

m represents an integer of 1, 2 or 3, is preferably either 2 or 3, and is most preferably 3.

Among the alkoxy silanes represented by the formula (2) are preferred those in which $R^7$ is an alkyl group of 1 to 4 carbon atoms, $R^8$ is an alkyl group of 1 to 4 carbon atoms, and m is 2 or 3.

Among the alkoxy silanes represented by the formula (2) are more preferred those in which $R^7$ is a methyl group or an ethyl group, $R^8$ is a methyl group, and m is 2 or 3.

Representative examples of the alkoxysilane represented by the general formula (2) include the compounds shown below.

$(CH_3O)_3Si—H$
$(CH_3CH_2O)_3Si—H$
$(CH_3O)_2(CH_3)Si—H$
$(CH_3CH_2O)_2(CH_3)Si—H$
$(CH_3CH_2CH_2O)_3Si—H$
$(CH_3CH_2CH_2CH_2O)_3Si—H$
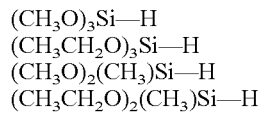
$(CH_3O)(CH_3)_2Si—H$
$(CH_3CH_2O)(CH_3)_2Si—H$ -Transition Metal Catalyst- Although there are no particular restrictions on the transition metal catalyst used in the present invention, platinum compounds, rhodium compounds, palladium compounds and ruthenium compounds are ideal. These compounds can be used singularly or a combination of two or more thereof. Platinum compounds are particularly preferred. Specific examples of these platinum compounds include platinum divinylsiloxane, platinum cyclic vinylmethylsiloxane, tris(dibenzylideneacetone)diplatinum, chloroplatinic acid, bis(ethylene)tetrachloro diplatinum, cyclooctadiene-dichloro platinum, bis(cyclooctadiene)platinum, bis(dimethylphenylphosphine)dichloro platinum, tetrakis(triphenylphosphine)platinum, and platinum-carbon.

The reaction temperature during synthesis of the organosilicon compound of the present invention is typically within a range from 50 to 150° C., and is preferably from 60 to 100° C. The reaction is typically continued until the raw materials are exhausted, and the reaction time is usually within a range from 30 minutes to approximately 10 hours, and is preferably from 1 to 5 hours.

The use of a solvent during the synthesis reaction is optional, and the reaction can be conducted either without a solvent, or in the presence of a solvent. If a solvent is used, then typical solvents include hydrocarbons such as pentane, hexane, heptane, octane, benzene, toluene or xylene, alcohols such as methanol or ethanol, ethers such as dibutyl ether, tetrahydrofuran or dioxane, ketones such as methyl ethyl ketone or methyl isobutyl ketone, esters such as ethyl acetate, amides such as dimethylformamide, and nitriles such as acetonitrile.

There are no particular restrictions on the synthesis method, and for example, the unsaturated group-containing compound having a β-ketoester structure represented by the formula (1) may be placed in a reaction vessel, the transition metal catalyst added, and the alkoxysilane represented by the formula (2) then added dropwise to the reaction vessel.

The molar ratio between the unsaturated group-containing compound having a β-ketoester structure represented by the formula (1) and the alkoxysilane represented by the formula (2), namely the molar ratio represented by [unsaturated group-containing compound of formula (1)]/[alkoxysilane of formula (2)], although not particularly limited, is typically within a range from 0.8 to 1.2, and is preferably from 0.95 to 1.05.

Following completion of the reaction, any solvent used may be removed by evaporation together with any unreacted raw materials, either at normal pressure or under reduced pressure. The temperature during this removal by evaporation may be set to an appropriate level, and is typically within a range from 60 to 150° C., and preferably from 60 to 100° C.

The organosilicon compound of the present invention obtained in this manner comprises a compound represented by a formula (3) shown below as the main component.

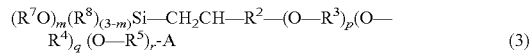
(3)

[wherein, $R^1$ to $R^5$, $R^7$, $R^8$, m, p, q, r and A are as defined above]

However, the organosilicon compound also includes compounds produced when an OH group generated by isomerization of the β-ketoester group and the alkoxy group of the alkoxysilyl group undergo an intramolecular or intermolecular exchange reaction. Accordingly, although the organosilicon compound of the present invention includes a compound of the formula (3) as the main component, the organosilicon compound is actually obtained as a mixture that also includes a variety of derivatives generated from the main compound.

Examples of the main component of the organosilicon compound of the present invention include the compounds shown below.

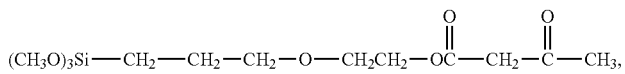

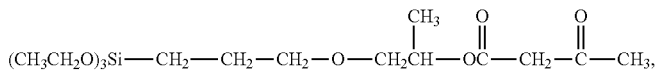

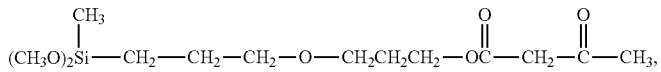

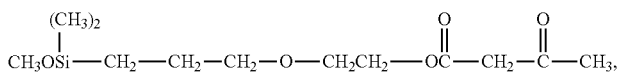

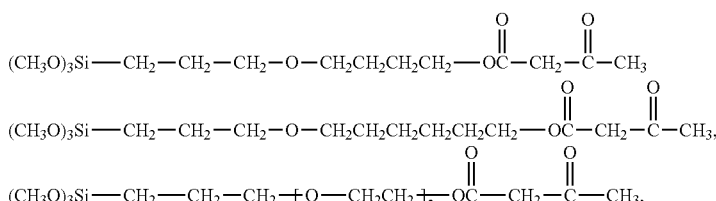

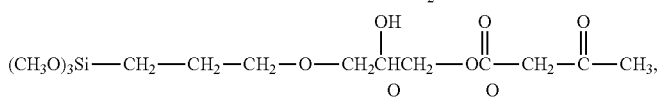

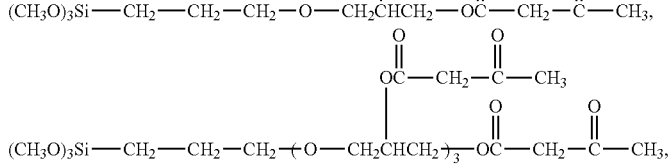

In terms of the compounds obtained when, as described above, an OH group generated by isomerization of the β-ketoester group and the alkoxy group of the alkoxysilyl group undergo an intramolecular or intermolecular exchange reaction, a multitude of compounds are possible and the mixture may be extremely complex, but specific examples include the compounds shown below.

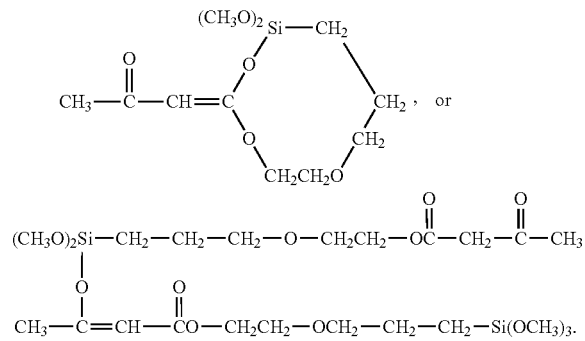

When the compound of the present invention is used as a composite material modifier, an adhesion improver, a surface treatment agent or a primer, the compound may be diluted with a solvent prior to use if desired. If a solvent is used, then the solvent used as a reaction solvent for diluting the reaction components may simply be used, or a solvent may be added to the compound of the present invention following completion of the reaction. There are no particular restrictions on the types of solvents that may be added following completion of the reaction, and examples include hydrocarbons such as pentane, hexane, heptane, octane, benzene, toluene or xylene, alcohols such as methanol or ethanol, ethers such as dibutyl ether, tetrahydrofuran or dioxane, ketones such as methyl ethyl ketone or methyl isobutyl ketone, esters such as ethyl acetate, amides such as dimethylformamide, and nitriles such as acetonitrile. Mixtures containing two or more different solvents may also be used.

-Applications-

When added to a resin or a rubber and mixed with an inorganic material, the organosilicon compound of the present invention can improve the dispersibility of the inorganic material. Examples of the resin include organic resins such as epoxy resins, phenolic resins, polyester resins, polyimide resins and polycarbonate resins, as well as silicone resins. Examples of the rubber include organic rubbers such as SBR, natural rubbers, acrylic rubbers and urethane rubbers, as well as silicone rubbers. Examples of the inorganic material include inorganic powders of silica, alumina, aluminum hydroxide, magnesium hydroxide, mica or glass.

The organosilicon compound of the present invention is also able to enhance the interfacial binding effect between an inorganic material such as silica, alumina or glass and an organic resin, and is therefore useful as a silane coupling agent for inorganic and organic composite materials.

Furthermore, when added to an adhesive or the like, the organosilicon compound of the present invention produces an adhesion improvement effect. Examples of the adhesive include epoxy adhesives, urethane adhesives and acrylic adhesives.

Moreover, the organosilicon compound of the present invention can also be added to a primer composition as a pressure-sensitive adhesion improver, and is effective in improving the adhesion of the composition to substrates.

[Pressure-Sensitive Adhesive Composition for Liquid Crystal Element]

Next is a detailed description of a pressure-sensitive adhesive composition for a liquid crystal element according to the present invention.

The pressure-sensitive adhesive composition for a liquid crystal element according to the present invention comprises an acrylic polymer that represents the main component, and an adhesion improver composed of the aforementioned organosilicon compound having a β-ketoester structure according to the present invention. The composition is described below in detail.

-(A) Acrylic Polymer-

The acrylic polymer of the component (A) has the effect of imparting pressure-sensitive adhesiveness to the composition of the present invention.

In the present invention, the term "acrylic polymer" describes a polymer (namely, a homopolymer or a copolymer) of an acrylic monomer. The term "acrylic monomer" includes both acrylic acid-based monomers and methacrylic acid-based monomers.

Examples of acrylic acid-based monomers include acrylic acid, acrylate esters and acrylamides. Examples of acrylate esters include alkyl acrylates such as methyl acrylate, ethyl acrylate and butyl acrylate.

Examples of methacrylic acid-based monomers include methacrylic acid, methacrylate esters and methacrylamides. Examples of methacrylate esters include alkyl methacrylates such as methyl methacrylate, ethyl methacrylate and butyl methacrylate.

In this description, terms such as "(meth)acrylic acid" and "(meth)acrylate" are generic terms that include acrylic acid and methacrylic acid, and acrylate and methacrylate respectively.

The acrylic polymer used in the present invention may be either a polymer produced from one of the above monomers, or a copolymer produced from two or more different monomers. Of the various possibilities, copolymers comprising an acrylic monomer having no functional groups and an acrylic monomer having a functional group are preferred. Examples of the functional group include a carboxyl group, hydroxyl group, amino group, epoxy group or amide group. The acrylic monomer having a functional group has at least one type of such functional groups.

Examples of the acrylic monomer having no functional groups include alkyl(meth)acrylates such as methyl(meth)acrylate, ethyl(meth)acrylate, isopropyl(meth)acrylate, butyl(meth)acrylate, 2-ethylhexyl(meth)acrylate, lauryl(meth)acrylate, stearyl(meth)acrylate, cyclohexyl(meth)acrylate, methoxyethyl(meth)acrylate and ethoxyethyl(meth)acrylate. These monomers may be used alone, or in combinations of two or more different monomers.

In the acrylic polymer used in the present invention, repeating structural units derived from the above type of (meth)acrylate ester having no functional groups preferably represent from 60 to 99% by mass, and more preferably 80 to 98% by mass, of all the structural units within the polymer.

Said acrylic monomer having a functional group comprises at least one acrylic monomer having, e.g., a carboxyl group, a hydroxyl group, an amino group, an epoxy group, an amide group, or a combination of two or more types thereof. Examples of the acrylic monomer having a functional group include acrylic acid, methacrylic acid, functional group-substituted alkyl(meth)acrylates such as β-carboxyethyl acrylate, 2-hydroxyethyl(meth)acrylate, 2-hydroxypropyl(meth)acrylate, chloro-2-hydroxypropyl(meth)acrylate and dimethylaminoethyl(meth)acrylate, as well as diethylene glycol mono(meth)acrylate, glycidyl(meth)acrylate, (meth)acrylamide, N-methylol(meth)acrylamide and N-ethylol(meth)acrylamide. These monomers may be used alone, or in combinations of two or more different monomers.

In the acrylic polymer used in the present invention, repeating structural units derived from the above type of acrylic monomer having a functional group typically represent from 1 to 20% by mass, and preferably 2 to 10% by mass, of all the structural units within the polymer.

The acrylic polymer used in the present invention may also include at least one type of repeating structural unit derived from a monomer other than the aforementioned acrylic monomer having no functional groups and the acrylic monomer having a functional group. Examples of these other units include repeating structural units derived from styrene-based monomers and repeating structural units derived from vinyl-based monomers.

Specific examples of the styrene-based monomers include styrene; alkylstyrenes such as methylstyrene, dimethylstyrene, trimethylstyrene, ethylstyrene, diethylstyrene, triethylstyrene, propylstyrene, butylstyrene, hexylstyrene, heptylstyrene and octylstyrene; halogenated styrenes such as fluorostyrene, chlorostyrene, bromostyrene, dibromostyrene and iodostyrene; and nitrostyrene, acetylstyrene and methoxystyrene.

Furthermore, examples of the vinyl-based monomers include vinylpyridine, vinylpyrrolidone, vinylcarbazole, divinylbenzene, vinyl acetate and acrylonitrile; conjugated diene monomers such as butadiene, isoprene and chloroprene; vinyl halides such as vinyl chloride and vinyl bromide; and vinylidene halides such as vinylidene chloride.

These other monomers may be used alone, or in combinations of two or more different monomers. In the acrylic polymer used in the present invention, repeating structural units derived from these other monomers typically represent from 0 to 20% by mass, and preferably from 0 to 10% by mass, of all the structural units within the polymer.

The acrylic polymer used in the present invention can be produced using conventional methods, for example, by charging a reaction vessel with the monomers described above, replacing the air inside the reaction system with an inert gas such as nitrogen gas, and then conducting the polymerization reaction by heating and stirring the reaction mixture, if necessary in the presence of a reaction initiator.

The use of a reaction solvent is optional, but usually an organic solvent is used. Examples of the solvent include aromatic hydrocarbons such as toluene and xylene, aliphatic hydrocarbons such as n-hexane, esters such as ethyl acetate and butyl acetate, alcohols such as n-propyl alcohol and i-propyl alcohol, and ketones such as methyl ethyl ketone, methyl isobutyl ketone and cyclohexanone.

Furthermore, in those cases where a reaction initiator is used, examples of initiators that may be used include azobisisobutyronitrile, benzoyl peroxide, di-t-butyl peroxide, and cumene hydroperoxide.

The reaction temperature for the polymerization reaction is typically within a range from approximately 50 to 90° C., and the reaction time is typically within a range from 2 to 20 hours, and preferably from 4 to 12 hours. In the above type of reaction, each monomer is added in a quantity equivalent to the quantity of repeating units derived from that monomer required within the target acrylic polymer. Furthermore, if a reaction solvent is used, then the quantity of the solvent is typically within a range from 50 to 300 parts by mass per 100 parts by mass of the total mass of monomers. The reaction initiator is typically added in a quantity within a range from 0.01 to 10 parts by mass.

By conducting a polymerization reaction in this manner, the acrylic polymer used in the present invention is obtained in the form of a solution or dispersion comprising 25 to 70% by mass of the (co)polymer dissolved or dispersed within the reaction solvent. In the present invention, the reaction solvent need not be removed from the reaction product, and the acrylic polymer dissolved or dispersed within the reaction solvent may be simply mixed with the other components.

The acrylic polymer used in the present invention has a weight average molecular weight that is typically within a range from 100,000 to 1,500,000, and preferably from 300,000 to 800,000. Other components such as inorganic fillers may be blended with the acrylic polymer, provided the inclusion of these other components does not impair the effects of the present invention.

-(B) Adhesion Improver-

In the composition of the present invention, the organosilicon compound having a β-ketoester structure described above is used as the component (B). This compound has a β-ketoester structure and a hydrolyzable silyl group, and includes a specific linking group comprising oxygen between the β-ketoester structure and the hydrolyzable silyl group. By including this specific linking group comprising oxygen, the compatibility of the compound with the acrylic polymer improves, and the distance between the β-ketoester structure and the hydrolyzable silyl group is increased, resulting in a more flexible structure. As a result, the adhesion achieved using this adhesion improver of the present invention, even under severe conditions such as conditions of high temperature and high humidity, is superior to that obtained when a pressure-sensitive adhesive using a conventional adhesion improver is used within a liquid crystal element. Moreover, it is thought that even if the produced liquid crystal element is exposed to these types of severe conditions, adhesive faults such as swelling or peeling of the polarizing plate or the laminate composed of a polarizing plate and a retardation plate are unlikely.

The adhesion improver of the component (B) is included in a quantity that is typically within a range from 0.001 to 5 parts by mass, and preferably from 0.01 to 2 parts by mass, per 100 parts by mass of the acrylic polymer of the component (A). If the quantity of the adhesion improver of the component (B) is too large, then the initial adhesive strength deteriorates, and swelling or peeling of the polarizing plate or the laminate composed of a polarizing plate and a retardation plate tends to become more prevalent under the liquid crystal element operating conditions. In contrast, if the quantity of the component (B) is too small, then when the composition is exposed to heat during the production process, the adhesive strength becomes overly powerful and the appropriate level of detachability is lost, meaning if an adhesion problem occurs, the composition cannot be readily detached, and if an attempt is made to detach the polarizing plate or the laminate composed of a polarizing plate and a retardation plate from the substrate, then not only is the liquid crystal cell prone to damage, but adhesive residues are more likely to remain on the substrate surface.

The acrylic polymer of the component (A) and the adhesion improver of the component (B) are preferably mixed immediately prior to use of the composition.

-Other Components-

The pressure-sensitive adhesive composition for a liquid crystal element according to the present invention comprises the acrylic polymer and the specific adhesion improver described above as essential components, but may also include other components as required.

Examples of other components that may be added to the pressure-sensitive adhesive composition for a liquid crystal element according to the present invention include tackifiers, plasticizers, cross-linking agents and dyes. Conventional materials may be used for these optional components. Moreover, the optional components may be used either alone, or in combinations of two or more different components.

A cross-linking agent, in particular, is preferably added to the pressure-sensitive adhesive composition for a liquid crystal element according to the present invention. Examples of cross-linking agents that can be used in the present invention include isocyanate-based compounds, epoxy-based compounds, amine-based compounds, metal chelate compounds and aziridine-based compounds.

Specific examples of isocyanate-based compounds that may be used as a cross-linking agent include tolylene diisocyanate, hydrogenated tolylene diisocyanate, trimethylolpropane tolylene diisocyanate adduct, trimethylolpropane xylylene diisocyanate adduct, triphenylenemethane triisocyanate and isophorone diisocyanate, as well as ketoxime block products or phenol block products of these isocyanate compounds.

Furthermore, specific examples of the epoxy-based compounds include bisphenol A-type and epichlorohydrin-type epoxy resins, ethylene glycol diglycidyl ether, polyethylene glycol diglycidyl ether, glycerol diglycidyl ether, glycerol triglycidyl ether, 1,6-hexanediol diglycidyl ether, trimethylolpropane triglycidyl ether, diglycidylaniline, diglycidylamine, N,N,N',N'-tetraglycidyl-m-xylenediamine and 1,3-bis(N,N'-diglycidylaminomethyl)cyclohexane.

Furthermore, specific examples of the amine-based compounds include hexamethylenediamine, polyethyleneimine, hexamethylenetetramine, diethylenetriamine, triethylenetetramine, isophoronediamine, amino resins and melamine resins.

Moreover, specific examples of the metal chelate compounds include compounds obtained by coordinating acetylacetone to a polyvalent metal such as aluminum, iron, copper, zinc, tin, titanium, nickel, antimony, magnesium, vanadium, chromium or zirconium, and compounds obtained by coordinating ethyl acetoacetate to the above polyvalent metals.

Moreover, specific examples of the aziridine-based compounds include N,N'-diphenylmethane-4,4'-bis(1-aziridinecarboxamide), N,N'-toluene-2,4-bis(1-aziridinecarboxamide), triethylenemelamine, bisisophthaloyl-1-(2-methylaziridine), tri-1-aziridinylphosphine oxide, N,N'-hexamethylene-1,6-bis(1-aziridinecarboxamide), trimethylolpropane-tri-β-aziridinylpropionate, and tetramethylolmethane-tri-β-aziridinylpropionate.

These cross-linking agents may be used either alone, or in combinations containing two or more different agents.

The cross-linking agent is used in a quantity that is typically within a range from 0.01 to 10 parts by mass, and preferably from 0.05 to 5 parts by mass, per 100 parts by mass of the resin component within the composition of the present invention. Because these cross-linking agents exhibit reactivity relative to the component (A) and the component (B) of the present invention, they are packaged separately and mixed with the component (A) and the component (B) immediately prior to use.

EXAMPLES

A description of specifics of the present invention is presented below based on a series of examples, although the present invention is in no way limited by the examples presented below.

Example 1

A 1-liter separable flask fitted with a nitrogen gas inlet, a thermometer, a Dimroth condenser and a dropping funnel was charged with 186 g (1.0 mols) of an unsaturated group-containing compound having a β-ketoester structure represented by a formula shown below:

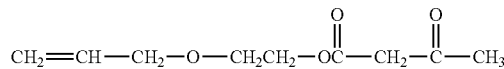

and 0.1 g of tris(1,3-divinyl-1,1,3,3-tetramethyl-disiloxane)-diplatinum(0) (the Karstedt catalyst), which has an equivalent platinum concentration of 2% by mass, and with the temperature set to 75° C., 122 g (1.0 mols) of trimethoxysilane represented by the formula $(CH_3O)_3Si-H$ was slowly added dropwise to the flask. This dropwise addition required 30 minutes. Following completion of the dropwise addition, reaction was continued for 3 hours at 75° C.

Following completion of the reaction, a gas chromatographic analysis was performed, confirming that the residual quantity of trimethoxysilane had fallen to not more than 2%.

Using a rotary evaporator, the thus obtained reaction product was concentrated under reduced pressure at 80° C. and 0.6 kPa, yielding 260 g of a pale brown transparent liquid. The viscosity of this liquid product was 9.75 $mm^2$/s at 25° C., and the refractive index was 1.4390 at 25° C. An infrared absorption spectral analysis of the liquid product was performed. The results of this infrared absorption spectral analysis are shown in Table 1.

Example 2

With the exceptions of replacing the unsaturated group-containing compound having a β-ketoester structure used in Example 1 with 300 g (1.0 mols) of an unsaturated group-containing compound having a β-ketoester structure represented by a formula shown below:

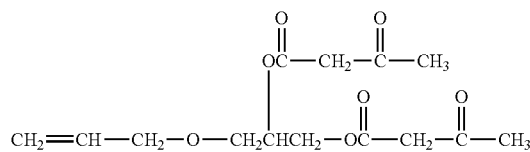

and altering the reaction time to 8 hours, reaction was conducted in the same manner as Example 1, and yielded 365 g of a brown transparent liquid.

Example 3

With the exceptions of replacing the unsaturated group-containing compound having a β-ketoester structure used in Example 1 with 200 g (1.0 mols) of an unsaturated group-containing compound having a β-ketoester structure represented by a formula shown below:

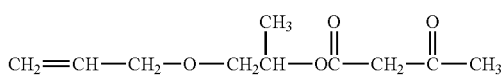

using 164 g of triethoxysilane as the alkoxysilane, and altering the reaction temperature to 85° C., reaction was conducted in the same manner as Example 1, and yielded 320 g of a pale yellow transparent liquid.

Example 4

With the exceptions of replacing the unsaturated group-containing compound having a β-ketoester structure used in Example 1 with 230 g (1.0 mols) of an unsaturated group-containing compound having a β-ketoester structure represented by a formula shown below:

using 230 g of toluene as a reaction solvent, and using 134 g (1.0 mols) of diethoxymethylsilane as the alkoxysilane, reaction was conducted in the same manner as Example 1, and yielded 305 g of a pale brown transparent liquid.

Example 5

A reaction vessel was charged with 43 parts by mass of n-butyl acrylate, 20 parts by mass of ethyl acrylate, 25 parts by mass of 2-ethylhexyl acrylate, 3 parts by mass of styrene, 7 parts by mass of acrylic acid, 2 parts by mass of 2-hydroxyethyl acrylate, 100 parts by mass of ethyl acetate, and 0.2 parts by mass of azobisisobutyronitrile, the air inside the reaction vessel was replaced with nitrogen gas, and the reaction mixture was then reacted under a nitrogen atmosphere, with constant stirring, for 2 hours at 63° C. Subsequently, 10 parts by mass of a solution prepared separately by dissolving 0.05 parts by mass of azobisisobutyronitrile in 10 parts by mass of ethyl acetate was added dropwise to the reaction vessel over 2 hours at 63° C.

The temperature within the reaction vessel was then raised to 72° C., and 10 parts by mass of an ethyl acetate solution of azobisisobutyronitrile prepared in the same manner as described above was added dropwise over 4 hours, yielding 220 parts by mass of an ethyl acetate solution of an acrylic polymer. The concentration of the acrylic polymer within the ethyl acetate solution was 45% by mass.

To the 220 parts by mass of the above reaction solution (equivalent to 100 parts by mass of the acrylic polymer) were added 0.1 parts by mass of the organosilicon compound mixture synthesized in Example 1 and comprising a β-ketoester group-containing alkoxysilane as the main component, and 2 parts by mass of a polyisocyanate compound (product name: Coronate L, manufactured by Nippon Polyurethane Industry Co., Ltd.) as a cross-linking agent, and the resulting mixture was stirred thoroughly to yield an adhesive composition of the present invention.

=Evaluation as Adhesive=

The adhesive composition was evaluated by measuring the detachability and implementability.

Detachability

Measurement of Initial Adhesive Strength

The adhesive composition prepared in the manner described above was applied to a polyester release film and dried to form a dried coating with a thickness of 25 μm. The adhesive composition coating was then transferred from the release film to one surface of a polarizing plate of thickness 0.20 mm, and left to stand for 7 days under conditions including a temperature of 23° C. and a humidity of 65%. Subsequently, the side of the polarizing plate having the adhesive composition coating formed thereon was bonded to the surface of a glass substrate, completing preparation of a sample. Bonding of the sample was completed by holding the laminated structure for 20 minutes at a temperature of 50° C. and under a pressure of 5 kg/cm².

In order to evaluate the adhesive strength between the polarizing plate and the glass substrate bonded in this manner, the initial adhesive strength (the adhesive strength following standing for one hour at 23° C.) was measured in accordance with JIS-Z-0237 and JIS-Z-0238.

Measurement of Adhesive Strength Following Aging Under Heat

A sample prepared in the same manner as that described above was left to stand for 15 hours at 80° C. and was then cooled to 23° C., and following standing at 23° C. for one hour, the adhesive strength was measured in the same manner as that described above.

Evaluation of Adhesive Residue

In the above measurements of the initial adhesive strength and the adhesive strength following aging under heat, a visual evaluation was made as to whether or not residual adhesive remained on the surface of the glass substrate when the polarizing plate was detached from the glass substrate.

Implementability

A sample prepared in the same manner as that described above was cut to dimensions of 20×30 cm², bonded to a substrate under the same conditions as those described above, and then either left to stand for 800 hours at 100° C. under dry conditions, or left to stand for a 800 hours under conditions including a temperature of 60° C. and a humidity of 90% RH, and the structure was then inspected visually for the occurrence of foaming within the adhesive composition coating and the occurrence of peeling between the polarizing plate and the substrate.

These results are shown in Table 1. In this example, the liquid crystal element comprising the polarizing plate bonded to the substrate surface exhibited favorable properties.

Example 6

With the exception of replacing the organosilicon compound mixture synthesized in Example 1 and comprising a β-ketoester group-containing alkoxysilane as the main component with the organosilicon compound mixture synthesized in Example 2 and comprising a β-ketoester group-containing alkoxysilane as the main component, an adhesive composition was obtained in the same manner as Example 5 The properties of the composition were evaluated in the same manner as that described for Example 5. The results are shown in Table 1.

Example 7

With the exception of replacing the organosilicon compound mixture synthesized in Example 1 and comprising a β-ketoester group-containing alkoxysilane as the main component with the organosilicon compound synthesized in Example 3 and comprising a β-ketoester group-containing alkoxysilane as the main component, an adhesive composition was obtained in the same manner as Example 5. The properties of the composition were evaluated in the same manner as that described for Example 5 The results are shown in Table 1.

Example 8

With the exception of replacing the organosilicon compound mixture synthesized in Example 1 and comprising a β-ketoester group-containing alkoxysilane as the main component with the organosilicon compound mixture synthesized in Example 4 and comprising a β-ketoester group-containing alkoxysilane as the main component, an adhesive composition was obtained in the same manner as Example 5 The properties of the composition were evaluated in the same manner as that described for Example 5. The results are shown in Table 1.

Comparative Example 1

With the exception of not using the β-ketoester group-containing alkoxysilane synthesized in Example 1, an adhesive composition was obtained in the same manner as Example 5. The properties of the composition were evaluated in the same manner as that described for Example 5. The results are shown in Table 1.

Comparative Example 2

With the exception of not using the organosilicon compound mixture synthesized in Example 1 and comprising a β-ketoester group-containing alkoxysilane as the main component, but instead using 0.1 parts by mass of an organosilicon compound comprising, as the main component, a β-ketoester group-containing alkoxysilane represented by a formula shown below:

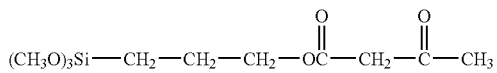

an adhesive composition was obtained in the same manner as Example 5. The properties of the composition were evaluated in the same manner as that described for Example 5. The results are shown in Table 1

15. An organosilicon compound having a β-ketoester structure represented by the formula:
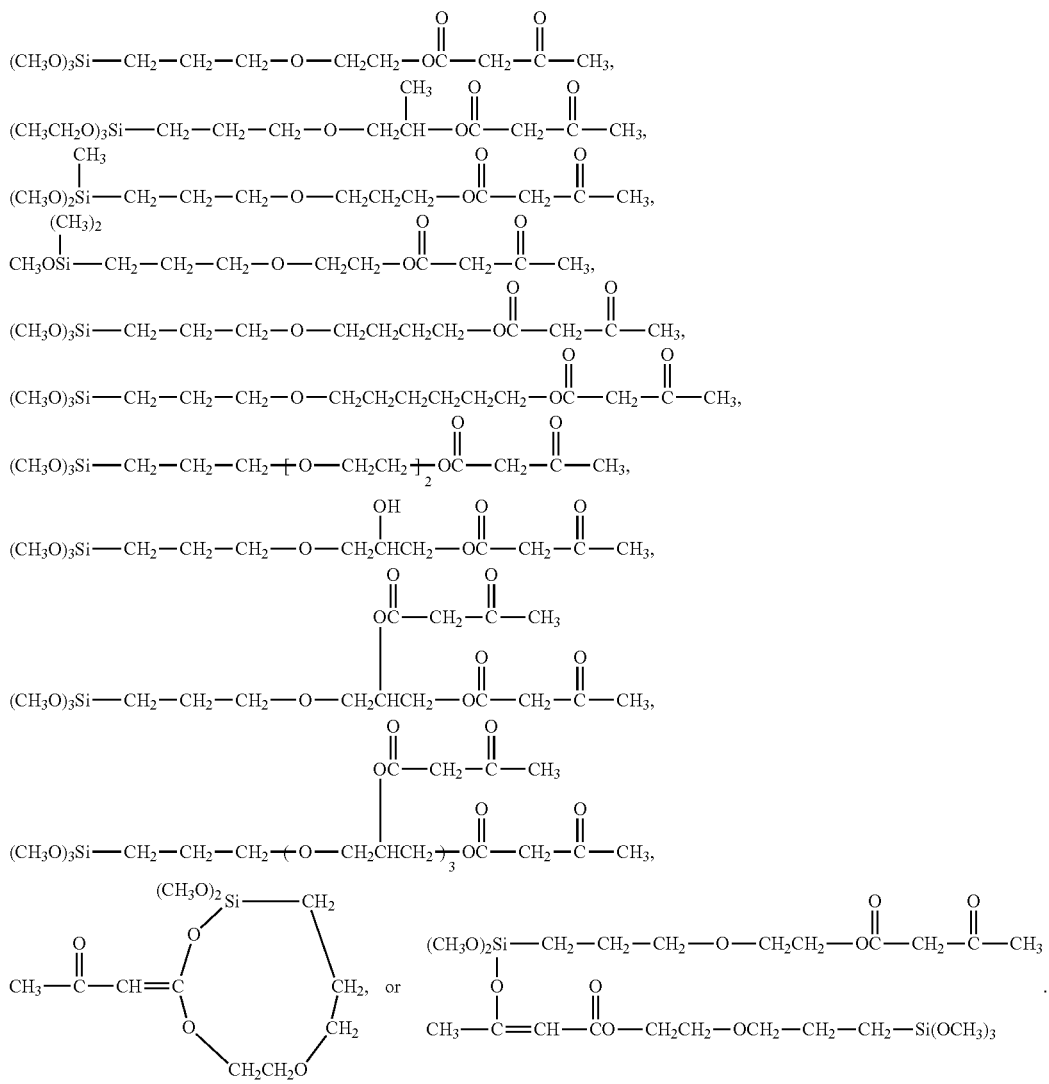

What is claimed is:
1. An organosilicon compound having a β-ketoester structure, obtained by conducting a reaction, in presence of a transition metal catalyst, between:
an unsaturated group-containing compound having a β-ketoester structure, represented by a formula (1) shown below:

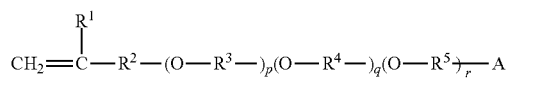

wherein
$R^1$ represents a hydrogen atom or a methyl group,
$R^2$ represents a divalent hydrocarbon group of 1 to 10 carbon atoms,
$R^3$ represents a divalent hydrocarbon group of 2 to 10 carbon atoms,
$R^4$ represents a divalent hydrocarbon group of 3 to 10 carbon atoms that is different from the divalent hydrocarbon group represented by $R^3$,
A represents a group represented by a formula (i) shown below:

wherein
$R^6$ represents an alkyl group of 1 to 10 carbon atoms, or a phenyl group that has or does not have a substituent,
$R^5$ represents a group represented by a formula (ii) shown below:

wherein
B represents OH or a group represented by the formula (i), and
p, q and r each represents, independently, an integer of 0 to 6, provided that p, q and r are not all zero, and

TABLE 1

|  |  | Example |  |  |  | Comparative example |  |
|---|---|---|---|---|---|---|---|
|  |  | 5 | 6 | 7 | 8 | 1 | 2 |
| Detachability | Initial adhesive strength (g/25 mm) | 1600 | 1650 | 1550 | 1450 | 1600 | 1550 |
|  | Adhesive residue | No | No | No | No | No | No |
|  | Adhesive strength after 10 hours at 80° C. (g/25 mm) | 1700 | 1800 | 1650 | 1600 | 2800 | 2000 |
|  | Adhesive residue | No | No | No | No | Yes | No |
| Implementability | 100° C. Foaming | No | No | No | No | No | No |
|  | dry Peeling | No | No | No | No | No | No |
|  | 60° C. Foaming | No | No | No | No | No | No |
|  | 90% RH Peeling | No | No | No | No | Yes | Yes | an alkoxysilane represented by a formula (2) shown below:

wherein $R^7$ and $R^8$ each represents, independently, a monovalent hydrocarbon group of 1 to 4 carbon atoms, and m represents 1, 2 or 3.

2. The organosilicon compound according to claim 1, wherein $R^2$ represents an alkylene group of 1 to 4 carbon atoms, $R^3$ represents an alkylene group of 2 to 4 carbon atoms, $R^4$ represents an alkylene group of 3 to 4 carbon atoms different from the alkylene group represented by $R^3$, A represents a group represented by a formula (i) wherein $R^6$ represents an alkyl group of 1 to 4 carbon atoms, a methylphenyl group or an ethylphenyl group.

3. The organosilicon compound according to claim 1, wherein $R^2$ represents a methylene group, $R^3$ represents an ethylene group, $R^4$ represents an i-propylene group or n-propylene group, and A represents a group represented by the formula (i) wherein $R^6$ represents a methyl group.

4. The organosilicon compound according to claim 1, wherein the compound represented by the formula (1) is one of the following compounds shown below:

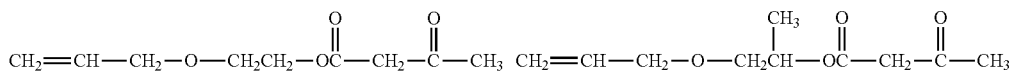

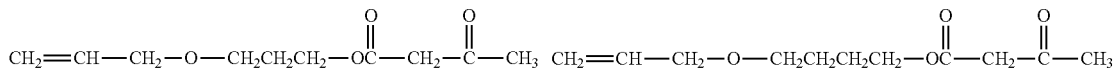

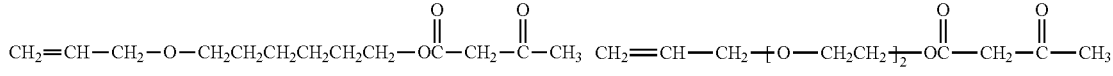

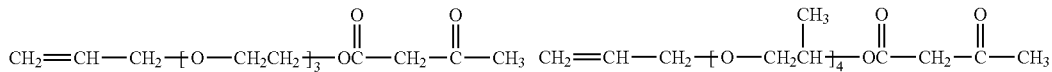

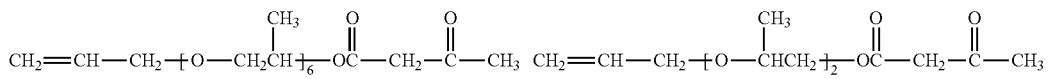

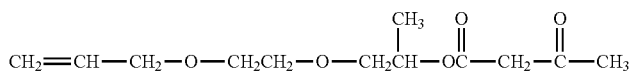

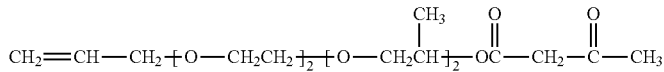

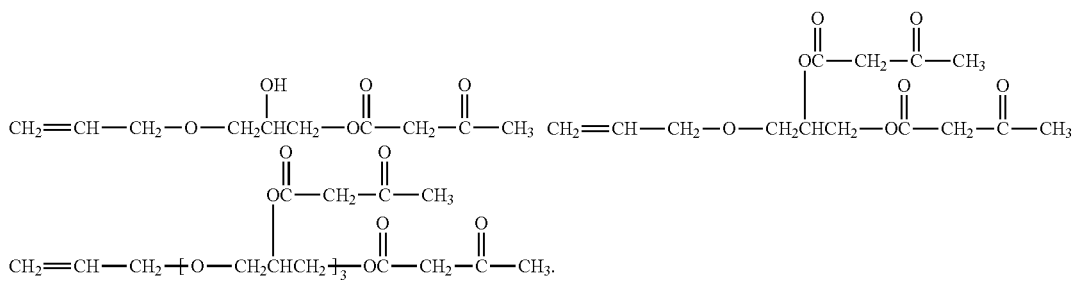

5. The organosilicon compound according to claim 1, wherein in the formula (2), $R^7$ is an alkyl group of 1 to 4 carbon atoms, $R^8$ is an alkyl group of 1 to 4 carbon atoms, and m is 2 or 3.

6. The organosilicon compound according to claim 1, $R^7$ is a methyl group or an ethyl group, $R^8$ is a methyl group, and m is 2 or 3.

7. The organosilicon compound according to claim 1, wherein the alkoxysilane represented by the formula (2) is one of the following compounds:

$(CH_3O)_3Si-H$, $(CH_3CH_2O)_3Si-H$, $(CH_3O)_2(CH_3)Si-H$, $(CH_3CH_2O)_2(CH_3)Si-H$, $(CH_3CH_2CH_2O)_3Si-H$, $(CH_3CH_2CH_2CH_2O)_3Si-H$, $(CH_3O)(CH_3)_2Si-H$, and $(CH_3CH_2O)(CH_3)_2Si-H$.

8. The organosilicon compound according to claim 1, wherein the transition metal catalyst is a platinum compound, a rhodium compound, a palladium compound, a ruthenium compound or a combination of two or more thereof.

9. The organosilicon compound according to claim 1, wherein the molar ratio represented by [unsaturated group-containing compound of formula (1)] / [alkoxysilane of formula (2)] is within a range from 0.8 to 1.2, and these compounds are reacted at a temperature from 50° C. to 150° C.

10. The organosilicon compound according to claim 1, comprising a compound represented by a formula (3):

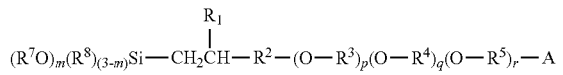

(3)

wherein, $R^1$ to $R^5$, $R^7$, $R^8$, m, p, q, r and A are as defined in claim 1.

11. A pressure-sensitive adhesive composition for a liquid crystal element, comprising:
(A) an acrylic polymer, and
(B) an adhesion improver composed of an organosilicon compound having a β-ketoester structure, obtained by conducting a reaction, in presence of a transition metal catalyst, between:
an unsaturated group-containing compound having a β-ketoester structure, represented by a formula (1) shown below:

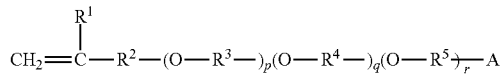

(1)

wherein
$R^1$ represents a hydrogen atom or a methyl group,
$R^2$ represents a divalent hydrocarbon group of 1 to 10 carbon atoms,
$R^3$ represents a divalent hydrocarbon group of 2 to 10 carbon atoms,
$R^4$ represents a divalent hydrocarbon group of 3 to 10 carbon atoms that is different from the divalent hydrocarbon group represented by $R^3$,
A represents a group represented by a formula (i) shown below:

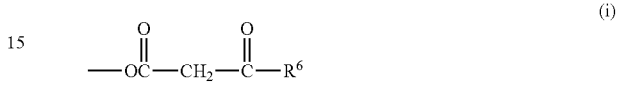

(i)

wherein
$R^6$ represents an alkyl group of 1 to 10 carbon atoms, or a phenyl group that has or does not have a substituent,
$R^5$ represents a group represented by a formula (ii) shown below:

(ii)

wherein
B represents OH or a group represented by the formula (i), and
p, q and r each represents, independently, an integer of 0 to 6, provided that p, q and r are not all zero and
an alkoxysilane represented by a formula (2) shown below:

$(R^7O)_m(R^8)_{(3-m)}Si-H$ (2)

wherein
$R^7$ and $R^8$ each represents, independently, a monovalent hydrocarbon group of 1 to 4 carbon atoms, and m represents 1, 2 or 3, wherein
a quantity of the adhesion modifier of component (B) is within a range from 0.001 to 10 parts by mass per 100 parts by mass of the acrylic polymer of component (A).

12. The composition for a liquid crystal element according to claim 11, wherein the acrylic polymer of component (A) is a copolymer formed from 60 to 99% by mass of an acrylic monomer having no functional groups, 1 to 20% by mass of an acrylic monomer having a functional group, and 0 to 20% by mass of other monomers capable of copolymerization with the acrylic monomers wherein a combination of the three types of monomer totals 100% by mass.

13. The composition according to claim 12, wherein said acrylic monomer having no functional groups comprises at least one alkyl (meth)acrylate, said acrylic monomer having a functional group comprises at least one acrylic monomer having a carboxyl group, a hydroxyl group, an amino group, an epoxy group, an amide group or a combination of two or more thereof, and said other monomer comprises a styrene-based monomer, a vinyl-based monomer or a combination thereof.

14. The composition according to claim 12, wherein $R^2$ is an alkylene group of 1 to 10 carbons, $R^3$ is an alkylene group of 2 to 10 carbon atoms, $R^4$ is alkylene group of 3 to 10 carbon atoms that is different from the alkylene group of $R^3$, and $R^6$ is an alkyl group of 1 to 10 carbon atoms, a phenyl group, a methylphenyl group or an ethylphenyl group.